United States Patent [19]

Shoji et al.

[11] 3,969,501

[45] July 13, 1976

[54] ANTIBIOTIC 342-14-I AND PRODUCTION THEREOF

[75] Inventors: Jun'ichi Shoji, Hirakata; Mikao Mayama, Ikeda; Shinzo Matsuura, Itami; Kouichi Matsumoto, Toyonaka; Yoshiharu Wakisaka, Takarazuka, all of Japan

[73] Assignee: Shionogi & Co., Ltd., Osaka, Japan

[22] Filed: May 23, 1975

[21] Appl. No.: 580,341

[30] Foreign Application Priority Data

June 19, 1974 Japan................................ 49-70712

[52] U.S. Cl............................... 424/118; 195/80 R
[51] Int. Cl.$^2$.......................................... A61K 35/74
[58] Field of Search....................... 424/118; 195/80

[56] References Cited
OTHER PUBLICATIONS

Miller, The Pfizer Handbook of Microbial Metabolites, McGraw-Hill Book Co., Inc., N. Y., N. Y., 1961, p. 393.

*Primary Examiner*—Jerome D. Goldberg
*Attorney, Agent, or Firm*—Wenderoth, Lind & Ponack

[57] ABSTRACT

A new antibiotic, 342-14-I, bein useful as a medicament and veterinary drug for inhibiting the growth of gram-positive pathogenic microorganism, and a process for preparing the same, being characterized by cultivating a 342-14-I-producing strain of microorganism belonging to the Genus Bacillus in an aqueous nutrient medium under aerobic conditions.

3 Claims, 1 Drawing Figure

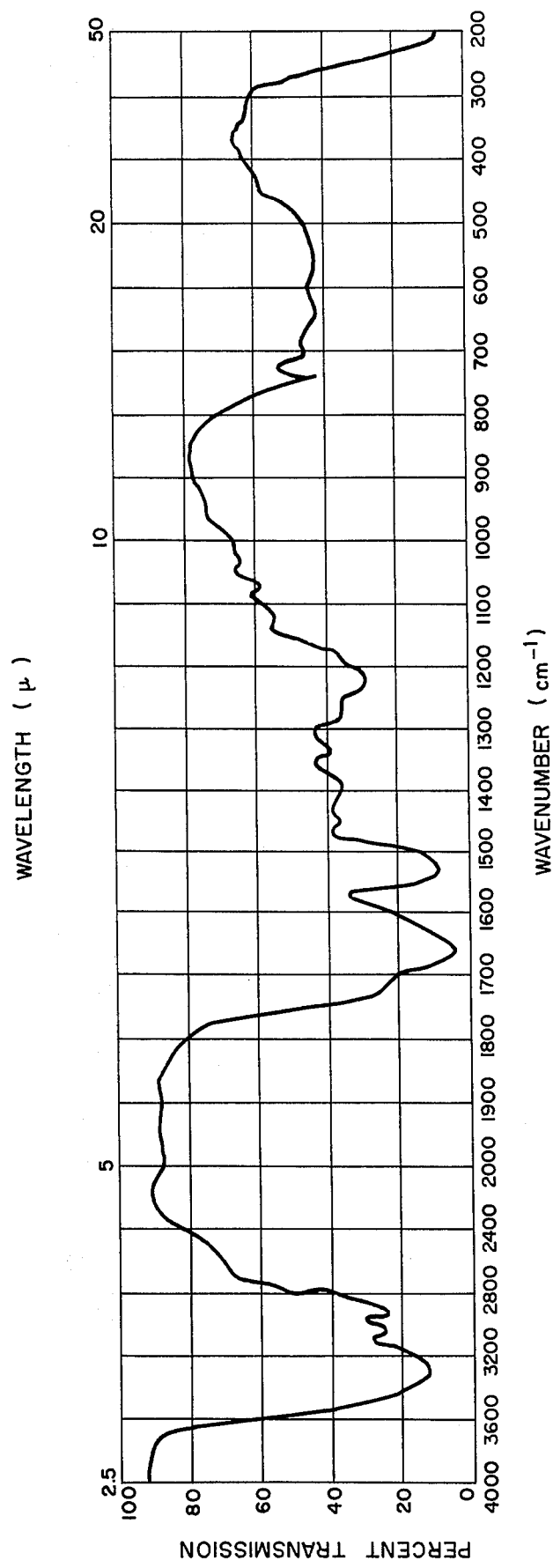

ANTIBIOTIC 342-14-I AND PRODUCTION THEREOF

The present invention relates to a novel antibiotic, 342-14-I, and production thereof.

In particular, the invention relates to a novel antibiotic, 342-14-I, having antibacterial activity, and to a method for producing the antibiotic, 342-14-I, characterized by cultivating an antibiotic 342-14I-producing strain of *Bacillus* in an aqueous nutrient medium under aerobic conditions and recovering 342-14-I from the culture broth.

In the course of a search for new fermentation products, it has newly been discovered that a microorganism belonging to *Bacillus brevis* species indexed No. 342-14 in the collection of Shionogi Research Laboratory, Shionogi & Co., Ltd., Osaka, Japan, and on deposit with the Fermentation Reserach Institute (a division of the agency of industrial science and technology, Japan) under the accession number FERM-P 2363 and with the American Type Culture Collection under the ATCC 21991, produces a new antibiotic, 342-14-I, when cultivated in an aqueous nutrient medium under aerobic conditions. The present invention has been accomplished on the basis of this discovery. Accordingly, the principal object of the invention is to provide a new and useful antibiotic which is active against gram-positive pathogenic microorganisms (including resistant bacteria). This and other objects which will be apparent to those conversant with the art to which the present invention pertains from the subsequent description, are achieved by the present invention.

*Bacillus brevis* No. 342-14 was isolated from a soil sample collected at Thailand and shows the following morphological characteristics.

I. Morphological characteristics (Culture on IM medium at 28°C for 1–4 days)
1. Form and arrangement: Rods with rounded ends, occurring singly or in mass.
2. Motility: Motile (active).
3. Flagella: *Peritrichous flagella*.
4. Size: Mainly 0.6–0.7 × 2.5–6.0 $\mu$.
5. Irregular form: Not observed.
6. Sporangia: Endospores distend the sporangium in a terminal or subterminal position; the sporangium is drumstick.
7. Endospore: Mainly 0.8 to 1.2 $\mu$, elliptical. The spore is easily stainable. The spore formation is relatively slow.
8. Gram staining: Gram-positive.
   IM medium: Soluble starch 0.2 %, Glycerol 0.2 %, Peptone 0.25 %, Beef meat extract 0.25 %, Yeast extract 0.25 %, Sodium chloride 0.3 %, Agar 1.0–1.2 %, pH 6.8

II. Cultural characteristics
A. Agar colonies (Plate culture on PB medium at 28°C for 1–7 days).
  1. Form: Circular.
  2. Surface: Smooth, shining (colonies cultured for a day). The shine becomes dull with aging.
  3. Edge: Entire
  4. Elevation: Convex.
  5. Consistency Butyrous.
  6. Optical density: Translucent.
B. Agar colonies (Slant culture on PB medium at 28°C for 1–7 days).
  1. Growth: Abundant.
  2. Form: Filiform.
  3. Chromogenesis of cell: Not chromogenic.
  4. Diffusible pigment: Not observed.
  5. Surface: Shining (Culture for a day), dully shining (Culture for over 2 days).
  6. Consistency: Butyrous to slightly viscid.
  7. Optical density: Translucent.
C. Liquid medium (Culture on GPB medium at 28°C for 1–7 days).
  1. Growth on surface: Sometimes ring on surface in liquid medium.
  2. Growth in medium: Growth moderate, uniform. A sediment develops slightly.
D. Gelatin stab (Culture on gelatin-yeast extract medium at 28°C for 1–8 days).
  1. Growth: Moderate.
  2. Liquefaction: Liquified.
E. Litmus milk (Culture at 28°C for 1–8 days).
  1. Litmus reaction: Negative.
  2. Peptonization: Positive (Culture for 4–8 days).
  3. Coagulation: Not observed.
   PB medium: Peptone 1.0 %, Beef meat extract 0.5 %, Sodium chloride 0.3 %, Agar 1.2–1.5 %, pH 6.8
   GPB medium: PB medium + 1 % Glucose.

III. Physiological characteristics.
1. Oxygen requirement: Aerobic (Culture on GPYB medium (agar stab) at 28°C for 1–4 days).
2. Temperature for growth: Optimum growth temperature lies around 28° C.
3. PH for growth: Optimum growth pH lies between 6.85 and 8.5 (IM medium).
4. Nitrate reduction: Negative.
5. O-F test: Oxidative type. Acid and gas are not produced. (GPYB medium + 0.015 % BCP)
6. Voges-Proskauer reaction: Negative.
7. Indol formation: Negative.
8. $H_2S$ formation: Negative (Difco Peptone Iron Agar).
9. Hydrolysis of starch: Negative.
10. Utilization of citrate: No growth on Koser's and Christensen's medium.
11. Oxidase test: Positive (PB medium).
12. Catalase activity: Positive (PB medium).
13. Tyrosinase activity: Negative.
14. Utilization of carbohydrates (Culture at 28°C for 1–7 days).

| Carbohydrate | °Synthetic medium Growth | Gas | Acid |
|---|---|---|---|
| Mannitol | − | − | − |

−: Growth does not occur. Gas and acid are not produced.

| Carbohydrate | °Nutrient medium Growth | Gas | Acid |
|---|---|---|---|
| L-Arabinose | + | − | − |
| D-Xylose | + | − | − |
| D-Glucose | + | − | + |
| D-Mannose | + | − | − |
| D-Galactose | + | − | − |
| D-Fructose | + | − | − |
| Sucrose | + | − | + |
| Maltose | + | − | + |
| Lactose | + | − | − |
| Trehalose | + | − | + |
| Starch | + | − | − |
| Glycogen | + | − | − |
| Inulin | + | − | − |
| Glycerol | + | − | − |
| Inositol | + | − | − |

| | -continued | | |
|---|---|---|---|
| Adonitol | + | − | − |
| Mannitol | + | − | − |
| Sorbitol | + | − | − |
| Salicin | + | − | − |
| α-methylglucoside | + | − | − |

+ : Good growth. Acid is produced.
− : Gas and acid are not produced.

15. Resistance to NaCl (Culture on GPB medium at 28°C for 1–5 days): Slight growth in 5 and 7.5 percent NaCl; No growth in 10 percent NaCl.

GPYB medium: Glucose 1.0 %, Peptone 0.5 %, Yeast extract 0.2 %, Beef meat extract 0.3 %, Agar 0.4 %, pH 6.6

From the above results, it is apparent that the strain should be classified as belonging to the Genus *Bacillus*. Further, comparison of the morphological, cultural, and physiological characteristics with many species of *Bacillus* described in Bree, R. S., Murray, E. G. D., & Smith, N. R., (1957) Bergey's Manual of Determinative Bacteriology, 7th ed. : Baltimore, The Williams & Wilkings Company, Gibbs, M.& Shapton, D. A., (1968) Identification Methods for Microbiologists: Academic press, London. New York, Laskin, A. I. & Iechevalier, H. A., (1972) Handbook of Microbiology, Vol. I : CRC Press, Ohio and other literature shows that in most of its properties the said strain is very similar to *Bacillus brevis*. Therefore, it is concluded that the strain of the present invention is of the *Bacillus brevis* species, and the microorganism of the present invention has been designated *Bacillus brevis* No. 342-14.

It is to be understood that for the production of 342-14-I, the present invention is not limited to the use of *Bacillus brevis* No. 342-14. It is especially desired and intended to include the use of natural or artificial mutants produced from the described organism or variants belonging to *Bacillus brevis* as far as they can produce the antibiotic, 342-14-I. The artificial production of mutants may be accomplished by a conventional operation such as X-ray or ultraviolet-ray irradiation, nitrogen mastards, 4-nitroquinoline N-oxide, N-methyl-N'-nitro-N-nitrosoguanidine and other mutagens.

In the present invention, the new antibiotic, 342-14-I, is produced during cultivation of the microorganism, e.g., *Bacillus brevis* No. 342-14, in an aqueous nutrient medium at a temperature of about 20 to about 37°C, preferably 25° to 35°C, under aerobic conditions, preferably submerged aerobic conditions. The composition of the nutrient medium may be varied over a very wide range. Essentially, what is required is a carbon source, a nitrogen source, and trace inorganic elements. Examples of suitable carbon sources are glucose, maltose, sucrose, xylose, fructose, galactose, inositol, mannitol, glycerin, dextrin, starch, organic acids, molasses, rice, wheat, potato, and the like. Suitable sources of nitrogen for the fermentation process include meat extract, peptone, soy bean meal, corn steep liquor, malt extract, yeast extract, peanut meal, aminosugar, cotton seed fluor, casamino acid, NZ amine, urea, ammonium sulfate, ammonium carbonate, ammonium chloride and the like. Examples of suitable sources of inorganic elements are mineral salts such as sodium chloride, potassium chloride, calcium carbonate, potassium phosphate and the like. The nutrient medium may or may not be adjusted to about pH 5.0–8.5 prior to inoculation of the microorganism. The pH tends to remain around the said level during the fermentation, but, if variations are encountered, a buffering agent such as calcium carbonate may be added to the medium to maintain the pH at about 5.0–8.5. In addition, if excessive foaming is encountered, anti-foaming agents such as vegetable oils, lard oil, and polypropyleneglycol may be added to the fermentation medium prior to or in the course of the fermentation. For a large scale of production, it is preferred to carry out the fermentation under submerged aerobic conditions. The maximum yields of the antibiotic, 342-14-I, can be attained within about 20 to about 100 hours, usually about 40 hours, of fermentation under optimum conditions of temperature and aeration.

After growth of the microorganism, the antibiotic, 342-14-I, can be recovered from the culture broth by a conventional manner. The cell may be obtained from the fermentation broth by using standard equipment such as filter-press and centrifuge, then antibiotic 342-14-I may be revovered from the cells by a solvent extraction procedure. As antibiotic 342-14-I is retained by the filtrate in small quantities, a solvent extraction procedure is preferably used to recover the antibiotic from the filtrate, or from the whole broth containing the cells. Suitable extraction solvents include dimethyl sulfoxide, aqueous methanol, aqueous ethanol, aqueous butanol, aqueous acetone and the like. For extraction of the antibiotic from a large volume of broth, however, an adsorption procedure is superior to a direct solvent extraction procedure. For instance, the whole broth may be filtered after the addition of an adsorbent, such as Hyflo Super Cel (diatomaceous earth), and the resultng cake of adsorbent and cell may be treated with a suitable organic solvent such as dimethyl sulfoxide, aqueous methanol, aqueous ethanol, aqueous butanol, or aqueous acetone to extract the antibiotic. The extract may be concentrated and, if necessary, a suitable solvent may be added to precipitate the crude active component.

The thus obtained crude active component may be further purified, if desired, by suitable operations such as reprecipitation, chromatography and the like. For example, reprecipitation may be carried out by dissolving the crude material in an organic solvent such as n-butanol, concentrating, and then adding a mixture consisting of ethyl acetate and ether (1 : 1 v/v) to the solution. The preferred chromatographic adsorbents are silica gel, silicic acid and the like.

Thus obtained 342-14-I may, when required, be converted into acid addition salts, ammonium salt, or metal salts suitable for pharmaceutical use, having low toxicity and desirable stability. Such a conversion can be effected in a conventional manner such as by treating the said 342-14-I with an acid, ammonium chloride or hydroxide in an appropriate solvent. Examples of the pharmaceutically acceptable acid-addition salts are hydrochloride, hydrobromide, hydroiodide, sulfate, phosphate, thiocyanate, oxalate, succinate, and nitrate. Examples of the metal salt are sodium salt, potassium salt, calcium salt, magnesium salt, aluminum salt, iron salt and the like.

The physical and chemical properties of antibiotic 342-14-I are as follows.

342-14-I (free form)

1. Elementary analysis: C, 54.63 %; H, 7.12 %; N, 14.81 %, O, 23.44 % (balance).

Hydrochloric acid salt of 342-14-I: C, 50.75 %; H, 6.82 %; N, 13.89 %, Cl, 5.05 %; O, 23.49 % (balance).

2. Melting point: The compound melts and decomposes at 190°–195°C.

Hydrochloric acid salt of 342-14-I: The compound melts and decomposes at 195°–200°C.

3. Molecular weight: about 1450 (estimated from amino acid analysis).

Hydrochloric acid salt of 342-14-I: about 1550 (estimated from amino acid analysis).

4. Specific optical rotation:

Hydrochloric acid salt of 342-14-I: $[\alpha]_D^{22.0} + 6.1 \pm 0.5°$ (c=1.036 %, in methanol)

5. Ultraviolet absorption spectrum: Hydrochloric acid salt of 342-14-I: $\lambda_{max}^{MeOH}$ : 274 m$\mu$ ($E_{1\ cm}^{1\ \%}$ 36), 283 m$\mu$ ($E_{1\ cm}^{1\ \%}$ 39), 290.5 m$\mu$ ($E_{1\ cm}^{10\%}$ 34)

6. Infrared absorption spectrum: Hydrochloric acid salt of 342-14-I(determined in KBr tablet): See FIG. 1

7. Solubility: Soluble in dilute acidic and alkaline solution. Hydrochloric acid salt of 342-14-I: Very soluble in methanol. Slightly soluble in ethanol. Insoluble in ethyl acetate, acetone and chloroform.

8. Color reaction: Ninhydrin reaction------------positive
Ehrlich's reaction------------positive 9. Color and form of the compound: Colorless powder, amphoteric substance.

10. Acid hydrolysis: Aspartic acid (1.92), threonine (0.62), glycine (1.23), valine (0.12), isoleucine (0.53), phenylalanine (0.65), tryprophane (0.77), 2,4-diaminobutyric acid (1.30), ammonia (0.76). (The numbers in parenthesis are $\mu$moles/mg).

An acid hydrolysate of the compound (342-14-I) was extracted with ether, the ether extract was methylated, then the methylated fatty acid containing in the extract was analyzed by gas chromatography. As a result the methyl ester of anteisononanoic acid was detected. Therefore, the antibiotic 342-14-I shows the formation of anteisononanoic acid by acid hydrolysis.

11. Behavior on thin-layer chromatography.

| Carrier | Solvent | Rf value |
|---|---|---|
| Silica gel GF | chloroform-ethanol-14 % aqueous ammonia (4 : 7 : 2 by volume) | 2.0 |
| Silica gel GF | chloroform-ethanol-10 % acetic acid (4 : 7 : 2 by volume) | 0.14 |
| Silica gel GF | n-butanol-acetic acid-water (3 : 1 : 1 by volume) | 0.40 |

Detection of the compound developed on a silica gel plate was conducted by bioautography using *Staphylococcus aureus* 209 P, ninhydrin reaction, and heat treatment of the plate sprayed by sulfuric acid.

The said chromatogram of 342-14-I prepared as described in Example 1 shows a single spot in each of the said solvent systems.

On the basis of the above physical and chemical properties, antibiotic 342-14-I is considered to be new acylpeptides.

Antibiotic 342-14-I shows activity against a variety of microorganisms. The in vitro antimicrobial activity of 342-14-I was determined by the agar plate dilution method. The results are shown in Table 1.

Table 1

| Test microorganism | Minimum inhibitory concentration (mcg/ml) |
|---|---|
| *Bacillus subtilis* PCI 219 | 6.25 |

Table 1-continued

| Test microorganism | Minimum inhibitory concentration (mcg/ml) |
|---|---|
| *Bacillus anthracis* | 6.25 |
| *Staphylococcus aureus* FDA 209P JC-1 | 3.13 |
| *Staphylococcus aureus* 80257 | 6.25 |
| *Staphylococcus aureus* Smith | 6.25 |
| *Streptococcus pyogenes* C-203 | 3.13 |
| *Diplococcus pneumoniae* type I (*Streptococcus pneumoniae*) | 6.25 |
| *Escherichia coli* NIHJ JC-2 | >50 |
| *Escherichia coli* 80750 | > |
| *Klebsiella pneumoniae* | >50 |
| *Salmonella typhimurium* | >50 |
| *Pseudomonas aeruginosa* PS-24 | >50 |

Medium: Modified Muller Hinton agar medium.

It is seen from Table 1 that antibiotic 342-14-I is highly active against gram-positive bacteria.

Acute toxicity studies on antibiotic 342-14-I were carried out in mice, and the $LD_{50}$ value was found to be 400–500 mg/kg intraperitoneally, and over 500 mg/kg subcateneously and orally. In addition, antibiotic 342-14-I is found to be highly active against *Staphylococcus aureus*, *Streptococcus pyogenes* and *Diplococcus pneumoniae* (*Streptococcus pneumoniae*) in a therapeutic experiment in mice with experimental infection. The results of a therapeutic experiment in mice with experimental infection are shown in Table 2.

Table 2

| Test microorganism | $ED_{50}$ mg/kg × 2 |
|---|---|
| *Staphylococcus aureus* Smith | 0.7 |
| *Streptococcus pyogenes* C-203 | 1.2 |
| *Diplococcus pneumoniae* type I (*Streptococcus pneumoniae*) | 3.5 |

Antibiotic: Hydrochloric acid salt of 342-14-I
Mouse: ICR Female 19-21g

Mice were infected with pathogenic bacteria by intraperitoneal injection. Antibiotic 342-14-I was administered subcutaneously to the mice at 1 and 5 hours after infection and survival of infected mice was examined on 7 days after infection.

The new antibiotic 342-14-I is useful as a medicament and veterinary drug for inhibiting the growth of gram-positive pathogenic miroorganism. It is also useful as a disinfectant.

The antibiotic 342-14-I and the pharmaceutical acceptable salts thereof of the present invention can be administered orally, subcutaneously, intravenously, or locally to human or animal in pharmaceutical conventional forms, e.g., injections, liquids suspensions, emulsions, ointments, or tablets with suitable carriers, stalbelizers, emulsifiers, preservatives and/or wetting agents, where a therapeutically effective amount of the active ingredient is contained. For example, the antibiotic 342-14-I and the pharmaceutical acceptable salts thereof can be administered orally, subcutaneously, or intravenously to human and domestic animal at a dosage of 0.1 mg to 100 mg per kg body weight.

The following examples are given solely for the purpose of illustration and are not to be construed as limitations of the present invention, many varitations of which are possible.

EXAMPLE 1

*Bacillus brevis* No. 342-14 (ATCC No. 21991) is inoculated to 100 ml of an aqueous nutrient medium (pH 7.0) composed of 1.0 % of glucose, 0.5 % of glycerin, 1.0 % of peptone, 0.5 % of meat extract and 0.3 % of sodium chloride, contained in 500 ml shaking flask (Sakaguchi flask). The cultivation is performed at 28°C for 2 days under shaking. The thus cultured broth is used as inoculum.

130 ml of an aqueous nutrient medium (pH 7.0) composed of 1.0 % of glucose, 0.25 % of glycerin, 0.25 % of peptone, 1.0 % of soy bean meal and 0.3 % of sodium chloride, contained in 500 ml shaking flask (Sakaguchi flask) is sterilized and inoculated with the inoculum (5 ml) prepared above. The cultivation is performed at 28°C for 4 days under shaking.

n-Butanol (2.5 l) and methanol (2.5 l) are added to about 5 liters of the cultured broth (containing the cells), and filtered. The obtained filtrate is concentrated under reduced pressure until it becomes two phase. The concentrated solution is adjusted to pH 8.0 and extracted twice with 500 ml of n-butanol. The n-butanol extract is extracted three times with 300 ml of water being adjusted to pH 2.0 or pH 3.0. The antibiotic 342-14-I remains in the butanol phase. The butanol phase is concentrated under reduced pressure. Ethyl acetate is then added to the concentrated solution to obtain the crude substance of 342-14-I (300 mg).

The crude substance is applied to a silica gel GF plate (thickness: 750 $\mu$, 100 × 20 cm) and developed with solvent consisting of chloroform, ethanol and 14 % aqueous ammonia (4 : 7 : 2 by volume). The part containing 342-14-I on the silica gel plate is extracted with the solvent consisting of methanol and water (1 : 1 by volume) being adjusted to pH 2.0 with dilute hydrochloric acid. The extract is concentrated under reduced pressure. The concentrate is applied to a silica gel GF plate (thickness: 750 $\mu$, 100 × 20 cm) and developed with solvent consisting of chloroform, ethanol and 1 % aqueous acetic acid (4 : 7 : 2 by volume). The part containing 342-14-I on the silica gel plate is extracted with the solvent consisting of methanol and water (1 : 1 by volume) being adjusted to pH 2.0 with dilute hydrochloric acid. The extract is concentrated, then extracted twice with n-butanol (pH 2.0). The n-butanol extract is washed with a small amount of water being adjusted to pH 7.0 by sodium bicarbonate, and then washed with distilled water. Concentration of the n-butanol solution under reduced pressure gives 342-14-I (about 100 mg) (free form) as a colorless amorphous powder.

What is claimed is:

1. An antibiotic, 342-14-I, effective in inhibiting the growth of gram-positive microorganism, the said antibiotic being a colorless amphoteric powder which melts and decomposes at 190°–195°C; contains the elements carbon, hydrogen, nitrogen and oxygen in substantially the following proportions by weight:

| Carbon | 54.63 % |
| --- | --- |
| Hydrogen | 7.12 % |
| Nitrogen | 14.81 % |
| Oxygen | 23.44 % (balance): | has a hydrochloric acid salt with an optical rotation of $[\alpha]_D^{22.0} + 6.1 \pm 0.5°$ (c=1.036 %, in methanol); has a molecular weight of about 1450 (estimated from amino acid analysis); shows the formation of aspartic acid, threonine, glycine, valine, isoleucine, phenylalanine, tryprophane, 2,4-diaminobutyric acid, ammonia and anteisononanoic acid by acid hydrolysis; has a hydrochloric acid salt with ultraviolet absorption (in methanol) at 274, 283 and 290.5 m$\mu$; and has a hydrochloric acid salt with an infrared absorption spectrum as in the attached drawing, FIG. 1.

2. A process for producing the antibiotic 342-14-I as defined in claim 1, which comprises cultivating the antibiotic 342-14-I-producing strain of *Bacillus brevis* No. 342-14, ATCC 21991 in an aqueous nutrient medium at a temperature from about 20° to 37°C for about 20 to about 100 hours under aerobic or submerged conditions and isolating the accumulated antibiotic 342-14-I from the cultured broth.

3. The process claimed in claim 2, wherein the isolation of the antibiotic 342-14-I is carried out by filtering the cultured broth, and extracting both the cell and the filtrate with a suitable solvent.

* * * * *